United States Patent

Gueret

[11] Patent Number: 5,904,151
[45] Date of Patent: May 18, 1999

[54] APPLICATOR FOR FRIABLE PRODUCT AND APPLICATION UNIT COMPRISING SUCH AN APPLICATOR

[75] Inventor: Jean-Louis H. Gueret, Paris, France

[73] Assignee: L'Oreal, Paris, France

[21] Appl. No.: 08/962,540

[22] Filed: Oct. 31, 1997

[30] Foreign Application Priority Data

Oct. 31, 1996 [FR] France .................................. 96 13360

[51] Int. Cl.$^6$ ................................................. A45D 33/00
[52] U.S. Cl. ......................... 132/293; 132/317; 132/320; 401/266; 206/581
[58] Field of Search .................................. 132/293, 286, 132/294, 295, 298, 318, 317, 320; 401/266, 200, 19; 220/281, 323, 4.22, 4.24, 608; 510/140; 206/581, 823

[56] References Cited

U.S. PATENT DOCUMENTS

| 1,460,607 | 7/1923 | Routson ................................... 220/281 |
| 1,524,008 | 1/1925 | Anastasia ................................ 401/266 |
| 1,665,788 | 4/1928 | Meyer .................................... 206/581 |
| 1,748,008 | 2/1930 | Barnowitz .............................. 132/293 |
| 1,899,386 | 2/1933 | Flosi ...................................... 401/200 |
| 2,234,558 | 3/1941 | Huston . |
| 2,450,919 | 10/1948 | Runnels ................................... 401/19 |
| 2,851,041 | 9/1958 | Grosso .................................... 206/581 |
| 3,332,429 | 7/1967 | Bates . |
| 3,664,353 | 5/1972 | Childress, Jr. .......................... 132/293 |
| 4,826,014 | 5/1989 | Schefer .................................. 206/581 |

FOREIGN PATENT DOCUMENTS

| 0526300 | 2/1993 | European Pat. Off. . |
| 53605 | 6/1946 | France . |
| 1272557 | 8/1961 | France ................................... 132/293 |
| 1272557 | 1/1962 | France . |
| 2086849 | 5/1982 | United Kingdom . |

*Primary Examiner*—Gene Mancene
*Assistant Examiner*—Pedro Philogene
*Attorney, Agent, or Firm*—Oblon, Spivak, McClelland, Maier & Neustadt, P.C.

[57] ABSTRACT

An applicator (1) for a friable product (P) has a resiliently deformable element (2) of which at least one side constitutes a surface (6) for applying the product. The resiliently deformable element has at least one hole (9) opening out on the application surface (6) and delimiting at least one recess (4) wherein the product is fixedly disposed. The product has at least one free surface (5). The resiliently deformable element is capable of selectively passing from a rest position, wherein the free surface (5) is situated at the level of, or below, the application surface (6), to an application position wherein the resiliently deformable element (2) is at least partially compressed along the axis (A) and in which the said free surface (5) is substantially at the level of the application position (6).

22 Claims, 5 Drawing Sheets

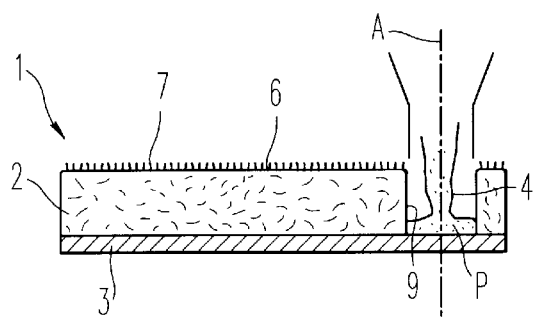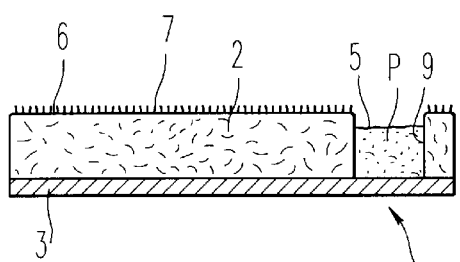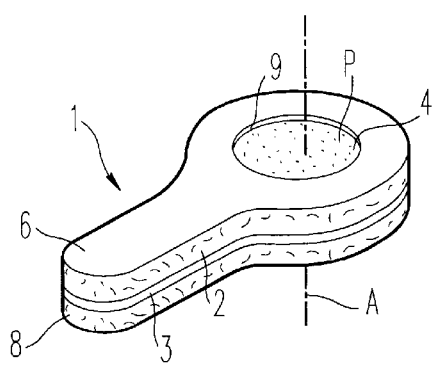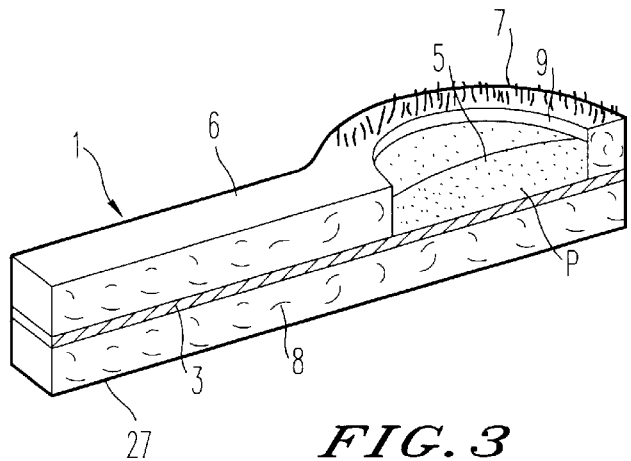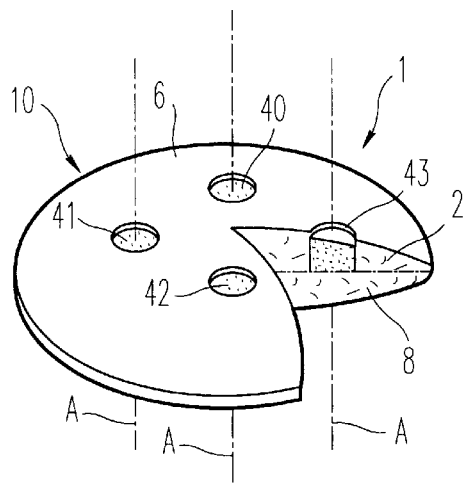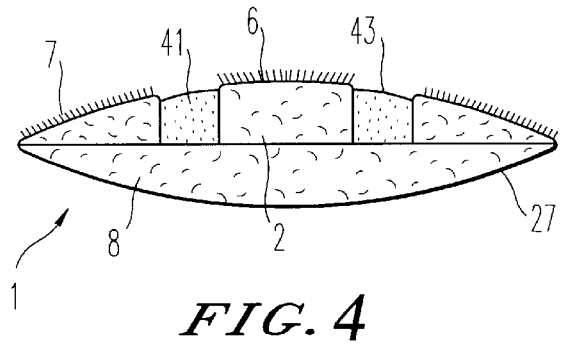

# APPLICATOR FOR FRIABLE PRODUCT AND APPLICATION UNIT COMPRISING SUCH AN APPLICATOR

BACKGROUND OF THE INVENTION

1. Field of the Invention

The present invention concerns an applicator of the type for applying a make-up product. Such an applicator may be used in particular for applying blusher, eye-shadow, cheek rouge, lipstick, foundation cream, care cream, suntan lotion or a hair product. More generally, it may be used for the application of any friable product. The invention also concerns a casing-type application unit comprising at least one applicator in accordance with the invention.

2. Description of the Related Art

To date, various types of applicators have been known for applying make-up products. There are known, inter alia, "matchstick" or "Q-tip" type applicators taking the form of a stem having one end charged with cosmetic products by immersion or by spraying. This first category of known applicators has the drawback of depositing too much of the product during application. Moreover this type of applicator does not allow the applied product to be softened. Finally, the configuration of these applicators generally makes them fragile.

Applicators are also known which have a cosmetic-type product pressed or compacted on the surface of the applicator. A major drawback of these applicators is their low capacity. Generally these applicators are used as samplers.

Finally, "puff" type applicators are used in combination with a compact having at least one pan in which the cosmetic products are cast or compacted. These powder compacts are relatively expensive.

FR-A-2642675 describes a dispenser for a solid or pasty product contained in a reservoir having a dispensing opening, the product being pushed towards the dispensing opening by means of a motor mechanism. According to this document, the edges of the dispensing opening are covered with a coating such as a flocked coating or a foam of small thickness so as to allow the product to be applied. The device described in this patent operates in a complicated manner and is relatively expensive to make.

There also exist other types of applicators of the type often used for applying shoe polish, in which the product to be applied is contained in a tube having mounted thereon a foam block which is pierced by a hole delimiting a duct communicating with the tube. In these applicators, the product is brought to the application surface by exerting pressure on (squeezing) the walls of the tube so as to cause the product to pass into the duct of the applicator and bring it to the application surface. Apart from their size, these devices are not suitable for products of the makeup type, mainly because of the difficulty of correctly dosing the product applied.

FR-A-1272557, U.S. Pat. No. 1,899,386 and U.S. Pat. No. 2,450,919 describe applicators for a product, generally in powder form, in which the powder is contained in a recess arranged in a foam block and the free end of the recess is covered by a screen in the form of a perforated sheet, a fabric or other porous material. In these devices the product is free in the recess thus formed, which renders the application of the dosed product difficult. Moreover, the orifices, pores or other holes which are arranged in the sheet obturating the hollow recess are liable to become quickly clogged up, which renders the device unusable. Finally, such devices are not suitable for products of a greater consistency, such as lipsticks.

The device described in U.S. Pat. No. 1,524,008, just like those described in U.S. Pat. No. 1,899,386 and U.S. Pat. No. 2,450,919, has a bottom forming an integral part of the foam block in which the recess is arranged. Soap contained in this recess is not joined to the recess, which confers an increasing axial mobility in the course of use. This mobility, in particular axial mobility, renders the application of the product very difficult to dose in a precise manner, this difficulty being accentuated since the bottom is not rigid or even semi-rigid. However, these problems of accuracy and metering of the application are not critical when the product is a soap, as in U.S. Pat. No. 1,524,008.

SUMMARY OF THE INVENTION

It is an object of the present invention to provide an inexpensive applicator lacking the conventional drawbacks mentioned above.

Another object of the invention is to provide an applicator of sufficient capacity to allow the applied product to be satisfactorily dosed.

Another object of the invention is to create an applicator which, apart from providing the application function, allows the applied product to be softened.

Yet another object of the present invention is to provide an applicator which contains, in an integrated manner, a reserve of the product to be applied, and affords a capacity, accuracy, quality and softness of application as satisfactory as those of more expensive applicator devices, in which the product is applied by means of an application device used in combination with a separate product reserve.

In accordance with a first aspect of the invention, these and other objects are obtained by creating an applicator for a friable product, comprising at least one resiliently deformable element, whereof at least one side has a surface for the application of the product, the resiliently deformable element having at least one hole with an axis opening out on the application surface and delimiting at least one recess in which the product is fixedly disposed, the product having at least one free surface. The resiliently deformable element is capable of selectively passing from a rest position in which the free surface is situated at the level or below the application surface, to an application position in which the at least one resiliently deformable element is at least partially compressed along the axis A, and in which the free surface is substantially at the level of the application surface.

Within the meaning of the present application, the expression "a hole with an axis opening out on the application surface" conveys the fact that the hole opens out on the application surface, and that it does so over the whole of the cross-section of the hole. In other words, in the application position it is not covered by a screen or other perforated or porous element capable of separating it from the surface on which the product is to be applied.

Similarly, the expression "fixedly disposed" conveys the fact that the product is substantially immovable axially in the applicator, and that the application is effected by the displacement (compression/decompression) of the surface of the resiliently deformable element which surrounds the product; this displacement selectively contributes to "uncovering" the product and to causing it to emerge substantially at the level of the application surface, with a view to its direct application to a surface to be treated. The product may be axially fixed, either by way of anchorage means provided on the bottom of the recess formed, for example by a rigid or semi-rigid core, or by lateral anchorage of the product in the structure of the material (the pores of a foam for example) constituting the resiliently deformable element, or both.

Thus, with a view to applying the product, the applicator is disposed on the surface to be treated. By exerting pressure on the applicator, the resiliently deformable element delimiting the recess is at least partially compressed so that the product comes into contact with the surface to be treated. At this moment, the product is applied to the surface, for example by small circular movements. By relaxing the pressure exerted on the applicator, the free surface of the product returns to the inside of the recess. Only the surface of the resiliently deformable element remains in contact with the surface to be treated. This free surface can then be used for completing the spreading out of the product without adding any product, and/or softening the product.

The fact that the product is fixedly held inside the recess contributes advantageously to obtaining a still more precise dosing of the applied product, by forming the bottom of the recess containing the product from a rigid or a semi-rigid core.

As mentioned above, the applicator has anchorage means so as to hold the product, at least axially, inside the recess. The anchorage means may be situated on the walls of the recess and or on the bottom of the recess. The product may be cast or compacted inside the compartment. It may also be cast or compacted beforehand in a cup and be subsequently mounted (with the cup) in the recess.

The foam block may be compressed to a height such that, irrespective of the product level in the recess, the application surface can be lowered to the level of the free surface of the product, so as to allow the application of substantially the whole of the product, the product being fixedly disposed in the recess. In other words, by compression of the resiliently deformable element to the level of the surface of the product in the cutout, the product is brought to the level of the application surface by lowering the application surface. The product cannot slide substantially inside the recess.

The recess may open out solely on a first application surface, or it may open out also on a second application surface on the side remote from the first application surface. In this latter configuration, the recess may contain a first and a second product, the first product being in the portion of the recess opening out on the first application surface, the second product being in the portion of the recess opening out on the second application surface. The first and second products may be of the same color or a different color. In this case, the anchorage of the product is effected on the side walls of the recess, for example in the pores of a foam with open cells. Indeed, during casting, the product penetrates into the pores of the foam situated in the vicinity of the lateral edges delimiting the recess. By hardening, the product held in the open cells of the foam fixes the product block in its recess.

The resiliently deformable element is advantageously mounted on a rigid or semi-rigid element, of which a first end defines a bottom for the recess and a second end defines a means for gripping the applicator.

Advantageously, the applicator has at least one foam block with open cells, half open cells, or closed cells. In the case of a foam with open or half open cells, the cells form lateral anchorage means for the product. By way of example, a foam of polyvinyl chloride (PVC), polyurethane, polyether, polyester or an SBR-type elastomer (synthetic butadiene rubber), NBR, silicone, nitrile etc. may be used. In an alternative, the fastening means are constituted by elements such as fins or ribs arranged in the floor of the recess.

In one embodiment, the applicator has two blocks of foam with open or half open cells, a first block defining at least one recess for the product, and a second block being disposed on the surface of the first block on the opposite side to the application surface. The two foam blocks are separated by a rigid or semi-rigid core, at least one of the blocks defining at least one recess for the product, and the core forming a bottom for the recess (or recesses).

In an alternative embodiment, the applicator has a block of foam with open or half open cells, of which one side on the side remote from the application surface is mounted on a rigid or semi-rigid core, the core forming a floor for the recess.

The application surface may be covered by a flocked coating, by a textile material or by a screen so as to promote the application of the product and to increase the softness of its application.

The product may be a blusher, cheek make-up, eyeshadow, lipstick, a foundation cream, a care cream, a suntan lotion or a hair product, etc.

According to a second aspect of the invention, an application unit includes a casing having a bottom, a lid capable of covering the bottom and at least one applicator mounted in the casing, the applicator being in accordance with the first aspect of the invention.

The bottom of the casing may define a bottom for the hole or holes of the applicator. Similarly, the lid may have an opening which, in the closed position of the lid on the bottom, is situated substantially opposite the hole of the applicator so as to allow the product to be cast into the applicator through the opening. After the product has been cast into the applicator, this opening may be covered by a transparent label to allow the color of the product in the casing to be displayed.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1A and 1B illustrate a first embodiment of an applicator in accordance with the invention, during and after casting of the product in the applicator;

FIGS. 2 and 3 are perspective and sectional views of a second embodiment of an applicator in accordance with the invention;

FIGS. 4 and 5 part cut away perspective and sectional views of a third embodiment of the applicator in accordance with the invention;

FIGS. 7A–7D illustrate a first embodiment of an application unit having an applicator in accordance with the invention, in which FIG. 7A shows the application unit before the first use, FIG. 7B shows the applicator unit after several uses, FIG. 7C shows the applicator unit applied to the skin and FIG. 7D illustrates a mode of filling the casing.

DETAILED DESCRIPTION OF THE PREFERRED EMBODIMENTS

Figure 6:
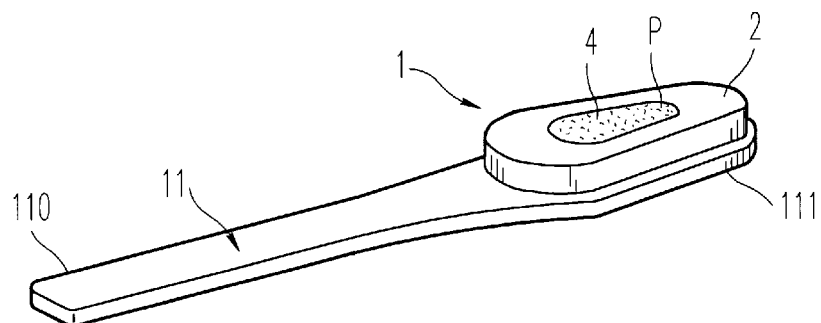
FIG. 6 is a perspective view of a fourth embodiment of an applicator in accordance with the invention.

The applicator 1 shown in FIGS. 1A and 1B has a foam block 2 mounted, for example, on a rigid or semi-rigid support 3. The foam block has a hole 9 with axis A defining a recess 4 for the product P, the rigid or semi-rigid support 3 forming a bottom for the recess. The height, density and resilience of the foam block or blocks are chosen in a suitable manner so that, in the rest position of the foam block, the product is substantially contained inside the recess 4 (at most, at the level of the application surface 6 before the first use of the product) and so that substantially the whole of the product contained in the applicator can be used up. Typically, for a lipstick, the product is cast over a height of from 2 mm to 14 mm for a recess whose depth when at rest is from 2 mm to 15 mm.

In the embodiment shown, the product is introduced and anchored in the recess by casting the product in a liquefied form which, after solidification, is transformed into a solid and friable product. The liquefied product may be in the form of a paste obtained by mixing a solid particulate phase with either an aqueous phase or with a binder, in particular a fatty phase in a solvent. It may also be in the form of a thermofusible wax-based product or a gel which is cast in its hot state. Depending on the type of composition chosen, the solidification is effected either by the evaporation of water or a solvent, by cooling or by a chemical reaction. The product may be an anhydrous paste cast in its hot state. Alternatively, in addition to colored pigments, fillers and binders, the product to be cast may contain hemihydrate calcium sulphate ($CaSO_4$, $\frac{1}{2}H_2O$) and a sufficient quantity of water for obtaining a castable mixture, the solidification occurring, after casting into the hole, by formation of dihydrate calcium sulphate ($CaSO_4$, $2H_2O$). In an alternative, the product may be contained in the recess in a compacted form.

The foam block may be constituted by a foam with open cells, half-open cells or closed cells. By way of example, the foam may be polyvinyl chloride (PVC), polyurethane, polyether, polyester or an SBR-type elastomer (synthetic butadiene rubber), NBR, silicone, nitrile etc. The foam can be mounted above a deformable, flexible wall molded from a thermoplastic or elastomeric material.

The bottom and/or the side walls of the recess may be impervious to the product P. The seal may be obtained by any known appropriate means, for example either by using a closed cell foam or by applying a coating which is impervious to the product P to the walls of the hole. Alternatively, the foam block is obtained by molding a material such as latex, the product resulting from the molding having perfectly leakproof sides, including the sides of the recess 4.

The bottom and/or the side walls of the recess 4 have means intended to allow the product to be fastened in the recess, and to fix it axially. In a preferred embodiment, the anchorage of the product in the recess is obtained by using a foam with open cells or half open cells. With such a configuration, when the product is being cast into the recess, it enters into the cells situated mainly in the vicinity of the sides of the recess. After solidification, the product P is fixed in the recess 4. As will be seen in greater detail below, the anchorage of the product P in the recess is preferably effected via the floor of the recess or, in any case, via the lower portion of the recess, so as not to substantially impede the compression of the resiliently deformable element.

The foam block 2 surface 6 for applying the product may be covered by a flocked coating 7. Alternatively, the application surface 6 may be covered with a different material such as a textile material or a screen, the nature of the application surface depending on the type of application of the product.

As shown in FIG. 1B, in the (non-compressed) rest position of the resiliently deformable element 2, the free surface 5 of the product P is situated at the level of, or preferably just below, the application surface (when the applicator has not yet been used) so that, in the rest position, the product is substantially protected by the foam surrounding it. As will be seen in greater detail below with reference to FIG. 6C, during use of the product the applicator is applied to the skin to produce (an at least partial) compression of the foam until the free surface of the product is substantially at the level of the application surface. The product is then in contact with the skin, the application surface 6 providing a good spread of the product on the skin. After the pressure exerted on the applicator has been relaxed, the user can subsequently soften the product, either with the application surface or with another surface of the applicator. Thus it is possible to dose and apply this product perfectly, depending on the pressure exerted on the applicator and on the duration during which the pressure is exerted. In the course of use, the level of the product in the recess decreases until the product has been substantially completely used up.

In an alternative, the resiliently deformable means is constituted by a bellows system surrounding the recess 4 in a leakproof manner, and one surface of the bellows is covered by an appropriate coating so as to impart the desired quality and softness to the application of the product. According to yet another alternative, the openings arranged in the resilient foam block may have a cross-section other than a circular cross-section. By way of example, the opening or openings may define one or several concentric recesses in the foam block.

FIGS. 2 and 3, to which reference will now be made, illustrate a second embodiment of the applicator in accordance with the invention, which can be used as an applicator of the eyeshadow type. It has a substantially circular portion in which is disposed the recess 4 for the product P, and a portion of an elongate shape for gripping the applicator either by hand or by a device such as a gripper (not shown). In this embodiment a second foam block 8 is disposed on the other side of the rigid or semi-rigid support 3 and has a surface 27 on the side remote from the application surface 6 which may be used, for example, to soften the product applied by means of the surface 6.

As illustrated in cross-section in FIG. 3, the surface 6 for applying the product has a flocked coating 7, or any other coating (a textile, elastomeric coating, etc.) which improves the softness and quality of the application.

In the embodiment illustrated in FIGS. 4 and 5, the applicator takes the form of a puff 1 with a domed shape on its two main sides and having two foam portions. The first foam portion 2 is pierced by several openings (4 in this case) defining a plurality of recesses 40, 41, 42, 43 capable of containing identical or different products. All the openings open out on the application surface 6 of the applicator. The second foam portion 8 of the applicator, which is advantageously separated from the first portion 2 by a rigid or semi-rigid plate (not shown), defines a bottom for the recesses 40, 41, 42, 43. In this configuration, the fastening of the product in the recesses 40, 41, 42, 43 may be effected via the bottom. The face 27 on the side remote from the application surface 6 may be used for softening the product applied by the application surface 6. As shown in FIG. 4, the application surface may also be covered by a flocked coating 7.

In the embodiment of FIG. 6 the applicator is mounted on one end of an element 11 of an elongate shape which is substantially planar. The element 11 forms, at one of its ends 111, a bottom for the recess 4 arranged in a foam block 2. The other end 110 of the element forms a gripping element to facilitate the manipulation of the applicator by the user. Preferably, the element 11 is constituted by a rigid or semi-rigid material.

Figure 7A:
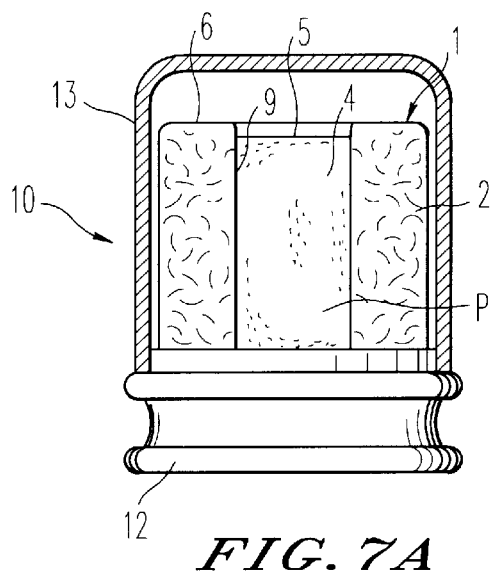

FIGS. 7A to 7D, to which reference will now be made, show an applicator mounted in a casing in accordance with one embodiment of the invention. This includes a bottom 12 on which there is mounted, for example by bonding, a foam block 2 having an opening which defines a recess 4 for the product P. The bottom of the casing also forms the bottom of the recess 4. A lid 13 is detachably mounted on the bottom. As shown in FIG. 7A, before the first use, the free surface 5 of the product is situated at the level of, or slightly below, the application surface 6. As mentioned above, the fastening of the product may be effected by means of open cells or half-open cells of the foam block 2. Alternatively, the fastening of the product, in particular at the bottom of the recess, may be effected by other means, such as fins, ribs or other appropriate reliefs arranged on the surface of the bottom of the casing on which the foam block is mounted.

Figure 7B:
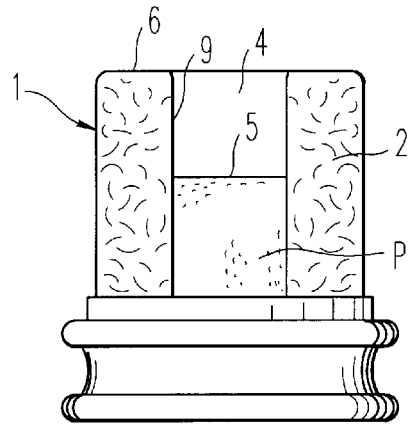

In FIG. 7B, the free surface 5 of the product P after several uses is situated substantially below the application surface 6. The product is thus protected inside the recess 4.

Figure 7C:
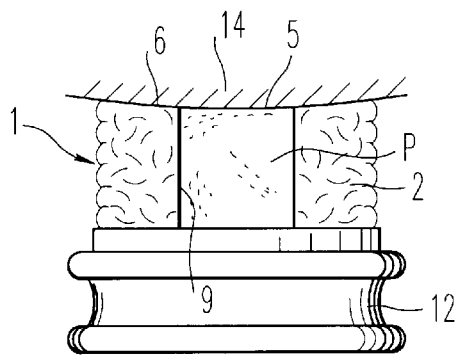

FIG. 7C shows the applicator applied to the skin 14. The foam block is then partially compressed so that free surface 5 of the product P is substantially at the level of the application surface 6. The product can then be applied in a dosed manner to the surface of the skin.

Figure 7D:
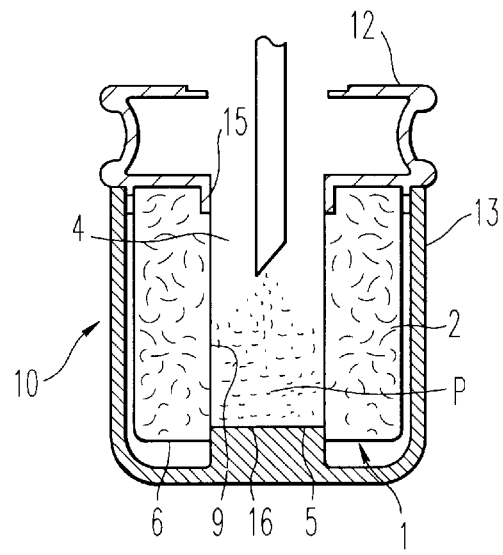

FIG. 7D illustrates a mode of filling the casing in accordance with the invention, in which filling is effect through the bottom of the casing through an opening 15 after the casing has been turned upside down. After filling, the opening 15 is obturated by a cap which may be welded, catch-engaged or bonded to the bottom. The lid 13 may be used as the bottom during the casting of the product. In this case, it has a central portion 16 with a diameter substantially equal to the diameter of the recess 4 so as to form a bottom during the casting step, and to limit the filling of the recess 4 to a level preferably slightly below the application surface 6 when the surface is at rest. Advantageously, before its first use, the free surface 5 of the product is 1 to 5 mm below the level of the application surface 6.

Figure 8A:
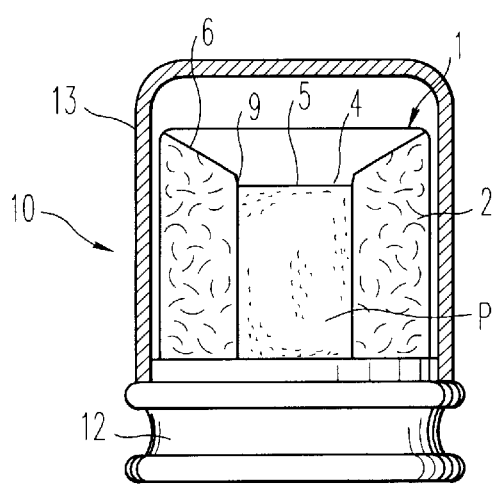
FIGS. 8A to 8E illustrate variants of the first embodiment.

In the variant of FIG. 8A, when at rest the application surface 6 has a frustoconical profile whose smallest diameter portion is adjacent to the recess 4. Such a configuration makes it possible to obtain variations and nuances in the application of the product. During the application of the product, the application surface is squashed and becomes substantially flat so as to follow the surface of the skin.

Figure 8B:
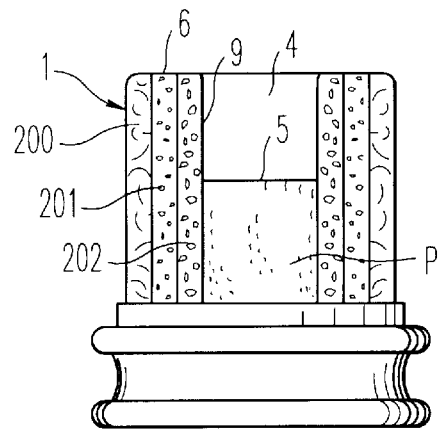

In the variant of FIG. 8B, the foam block is formed of a plurality of concentric portions 200, 201, 202 around the recess 4, it being possible for each of the blocks to have different hardnesses or densities so as to allow nuances in the application of the product.

Figure 8C:
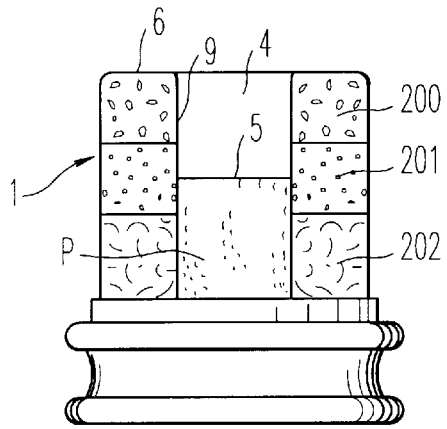

In the variant of FIG. 8C, the resiliently deformable element is a tube formed by a stack of superposed foam blocks, each of the blocks being traversed by a central hole. The blocks 200, 201, 202 are disposed so that their respective central holes are substantially aligned. As in FIG. 8B, each of the blocks may have different hardnesses and densities. The stack may be obtained by the molding or bonding of diverse stacked blocks.

Figure 8D:
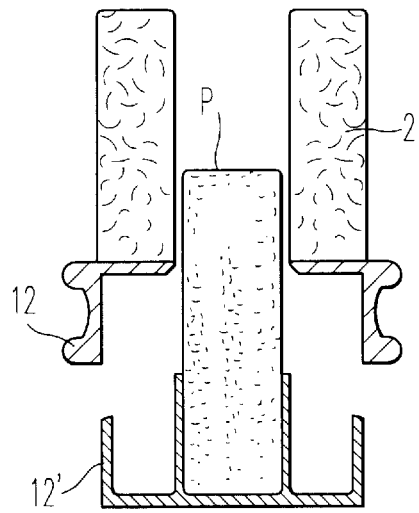

In the variant of FIG. 8D, the product is, for example, a lipstick mounted (for example cast) beforehand in a cup 12'.

Figure 8E:
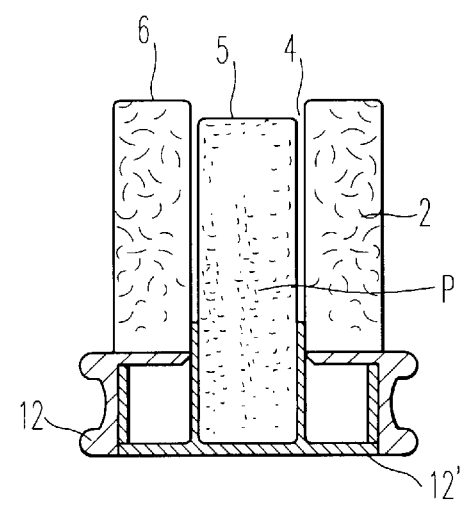

The resulting unit is fixedly mounted in the applicator through an opening formed in the bottom 12 of the applicator. The mounted unit is shown in FIG. 8E. The cup 12' may be welded, catch-engaged or bonded on the bottom 12. Advantageously, the cup 12' has means such as fins to allow the product to be anchored in the cup.

Figure 9:
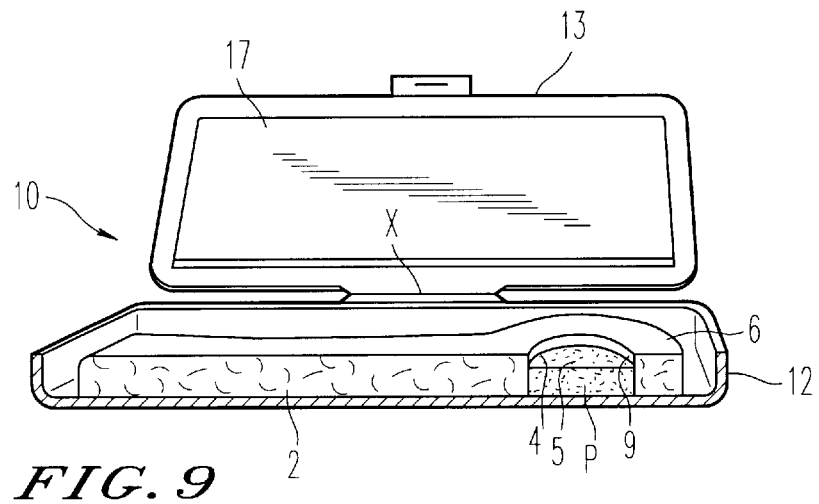
FIGS. 9 to 11 schematically illustrate perspective views of other embodiments of an application unit in accordance with the invention.

The compact of FIG. 9 has a lid 13 articulated to the bottom 12 around a hinge pin X. The internal surface of the lid 13 has a mirror 17. In accordance with this embodiment, the filling of the recess 4 is effected from the top, the bottom of the compact serving as the bottom for the recess 4.

Figure 10:
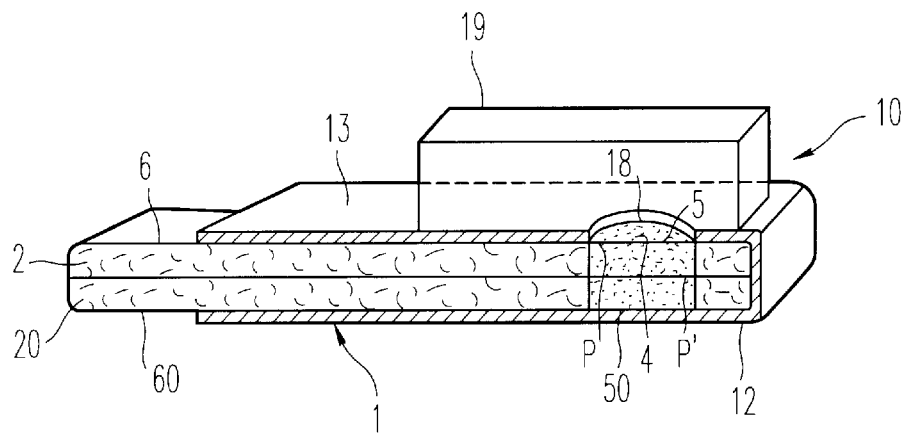

In the embodiment of FIG. 10, the applicator has two application surfaces 6 and 60. The applicator has two superposed foam blocks 2, 20 optionally separated by a rigid or semi-rigid core. The recess 4 passes through the two blocks 2, 20 and opens out both on an first application surface 6 and on the second application surface 60.

The compact takes the form of a casing, of which one part forms a bottom 12 and another part forms a lid 13. The lid has an opening 18 which, when the applicator is inserted in the casing, is situated substantially in alignment with the recess 4 so that filling may be effected by casting through the opening 18, the bottom of the casing defining a bottom for the recess during casting.

A first product P' may be cast in the portion of the recess opening out on the surface 60, while a second product P, e.g., of different color, may subsequently be cast in the portion of the recess opening out on the other application surface 6. Thus a two-sided applicator is obtained.

The axial fixing of the products P, P' is effected by anchoring the product in the open cells of the material in which the recess 4 is arranged. The casing may be made of a translucent material so as to display the color of the products contained in the applicator. Alternatively, a translucent label 19 is stuck onto the lid 13 so as to obturate the opening 18 after filling, and also to indicate the color of the product P.

Alternatively, the applicator is made by means of a single foam block whose thickness is chosen in an appropriate manner.

Figure 11:
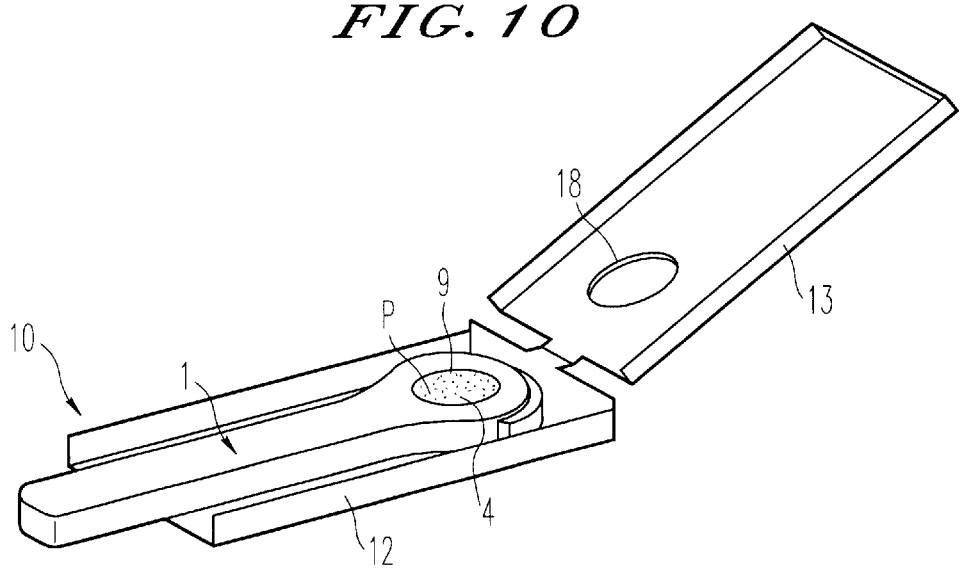

In the embodiment of FIG. 11, the lid 13 is articulated to the bottom 12. In the same way as for the embodiment of FIG. 9, the lid has an opening which, in the closed position of the lid 13 on the bottom 12, is substantially in alignment with the recess 4. The recess 4 can thus be filled through the opening 18.

Figure 12:
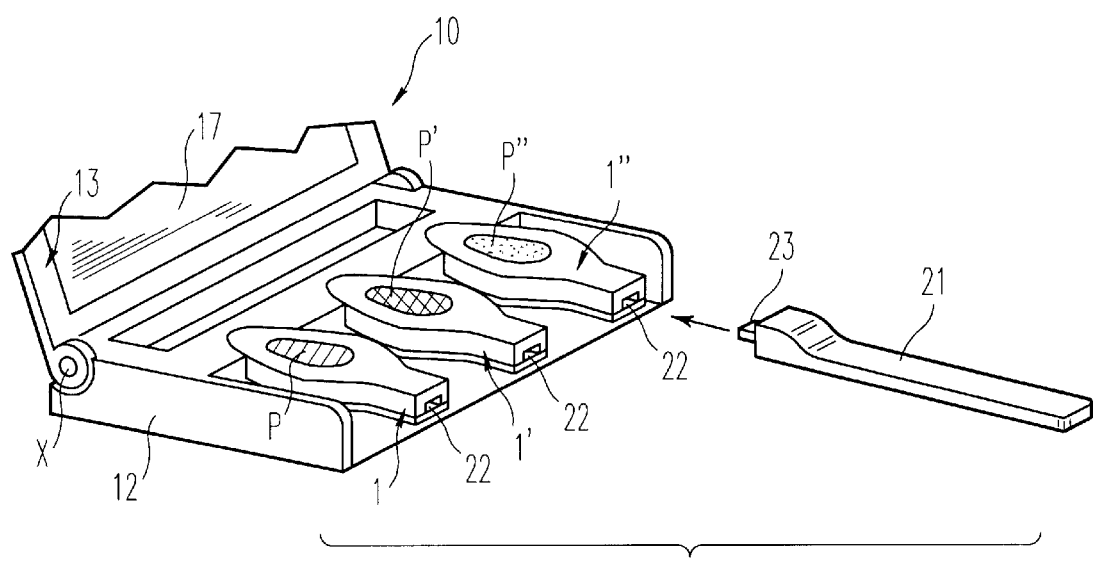
FIG. 12 is a partial perspective view of a compact having a plurality of applicators in accordance with the invention.

In FIG. 12, the application unit 10 has a plurality of applicators 1, 1', 1", each having a different product P, P', P". The unit is mounted inside a compact having a lid 13 articulated on a bottom 12 around a hinge pin X. The internal surface of the lid has a mirror 17. Each of the applicators has a female part 22 capable of cooperating with the male part 23 of a handle 21. A recess is arranged in the bottom of the compact 10 so as to receive the handle 21. Thus there is obtained a kit, for example a make-up kit, comprising a plurality of applicators which can be used with the same handle. The unit is compact, of small size and can be easily carried in a handbag.

The invention which has been described is particularly advantageous in that it creates an applicator of the make-up applicator type comprising, in an integrated way, a reserve of the product to be applied, and affording all the facilities and characteristics of conventional applicators in terms of capacity, quality, precision and softness of application.

Obviously, numerous modifications and variations of the present invention are possible in light of the above teachings. It is therefore to be understood that the invention may be practiced otherwise than as specifically described herein.

I claim:

1. An applicator for a friable product, comprising:
   a resiliently deformable element having an application surface for the application of a friable product, said resiliently deformable element having at least one hole opening out on the application surface over substantially the whole of the cross section of the hole and delimiting at least one open recess; and
   a friable product fixedly disposed in said recess, said product having a free surface positioned relative to said application surface such that said free surface is positioned no higher than said application surface when said resiliently deformable element is in an uncompressed state.

2. An applicator according to claim 1, wherein the product is cast or compacted in the recess.

3. An applicator according to claim 1, including a cup mounting the product in the recess.

4. An applicator according to claim 1, including a second surface on a side of said resiliently deformable element opposite said application surface.

5. An applicator according to claim 1, wherein said at least one hole opens out on said second surface which comprises a second application surface, said product having a second free surface positioned relative to said second application surface such that said second free surface is positioned no higher than said second application surface when said resiliently deformable element is in an uncompressed state.

6. An applicator according to claim 5, wherein said product in said recess comprises a first product portion having the first free surface and a second product portion having the second free surface.

7. An applicator according to claim 6, wherein said first and second products portions are of different colors.

8. An applicator according to claim 1, including a rigid or semi-rigid element defining both a bottom for said recess and a means for gripping said applicator.

9. An applicator according to claim 1, including anchorage means situated in the recess for fixing the product in the recess.

10. An applicator according to claim 1, wherein said resiliently deformable element comprises at least one foam block.

11. An applicator according to claim 10, wherein the at least one foam block has at least one of open cells and half-open cells, said cells forming the anchorage means.

12. An applicator according to claim 10, further comprising a rigid or semi-rigid core forming a bottom for said recess, wherein said at least one foam block comprises two blocks, a first of said blocks defining the recess, a second of said blocks being separated from said first block by said core and defining a softening surface for softening the product applied by means of the application surface.

13. An applicator according to claim 10, wherein said at least one foam block comprises plural blocks arranged concentrically around the recess.

14. An applicator according to claim 10, wherein said at least one foam block comprises a stack of blocks having substantially aligned holes to form the recess.

15. An applicator according to claim 1, wherein the application surface, when uncompressed, has a frustoconical profile whose smallest diameter is adjacent to the recess.

16. An applicator according to claim 1, including one of a flocked coating, a textile material and a screen covering the application surface.

17. An applicator according to claim 1, wherein the resiliently deformable element is formed by a foam of at least one of polyvinyl chloride (PVC), polyurethane, polyether, polyester, an SBR-type elastomer (synthetic butadiene rubber), NBR, silicone and nitrile.

18. An applicator according to claim 1, wherein said product is a at least one of a blusher, cheek make-up, eye-shadow, a foundation cream, suntan lotion and a hair product.

19. An application unit comprising:
    a casing having a bottom and a lid capable of covering said bottom; and
    at least one applicator mounted in the said casing and comprising a resiliently deformable element having an application surface for the application of a friable product, said resiliently deformable element having at least one hole opening out on the application surface over substantially the whole of the cross section of the hole and delimiting at least one open recess, and a friable product fixedly disposed in said recess, said product having a free surface positioned relative to said application surface such that said free surface is positioned no higher than said application surface when said resiliently deformable element is in an uncompressed state.

20. An application unit according to claim 19, wherein the bottom of the casing defines a bottom for each said recess of said applicator.

21. An application unit according to claim 19, wherein the lid has an opening which, in a closed position of the lid on the bottom, is situated substantially opposite the hole of the applicator so as to allow the product to be cast into the applicator through said opening.

22. An application unit according to claim 19, including a transparent label covering the opening of the lid so as to allow the color of the product in the casing to be displayed.

* * * * *